(12) United States Patent
Kashmirian et al.

(10) Patent No.: US 8,777,921 B2
(45) Date of Patent: *Jul. 15, 2014

(54) STERILE SAMPLING METHODS AND APPARATUS

(71) Applicant: Noble House Group Pty Ltd., Chelsea Heights (AU)

(72) Inventors: Avtar Singh Kashmirian, Kambah (AU); Stephanie M. Norrell, Herndon, VA (US); William Leonard Mobbs, Farrar (AU); Craig Douglas Wilson, Bondi Junction (AU)

(73) Assignee: Noble House Group Pty Ltd., Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/766,665

(22) Filed: Feb. 13, 2013

(65) Prior Publication Data

US 2013/0152707 A1 Jun. 20, 2013

Related U.S. Application Data

(63) Continuation of application No. 12/857,918, filed on Aug. 17, 2010, which is a continuation-in-part of application No. 10/990,820, filed on Nov. 17, 2004, now Pat. No. 7,785,304.

(30) Foreign Application Priority Data

Nov. 19, 2003 (AU) ................................ 2003906364

(51) Int. Cl.
 *A61B 19/00* (2006.01)
(52) U.S. Cl.
 USPC .......................................... 604/406; 604/317

(58) Field of Classification Search
 USPC .......................... 604/403–411, 415, 533–535
 See application file for complete search history.

(56) References Cited

U.S. PATENT DOCUMENTS

| 4,369,779 A | 1/1983 | Spencer |
| 4,439,188 A | 3/1984 | Dennehey et al. |

(Continued)

FOREIGN PATENT DOCUMENTS

| WO | WO/00/07642 | 2/2000 |
| WO | WO/02/089900 | 11/2002 |

(Continued)

OTHER PUBLICATIONS

PCT International Search Report and Written Opinion dated Dec. 10, 2004 issued in PCT/AU2004/001562 (WO2005/048842).

(Continued)

*Primary Examiner* — Melanie Hand
(74) *Attorney, Agent, or Firm* — Emily M. Haliday; Weaver Austin Villeneuve & Sampson LLP

(57) ABSTRACT

An apparatus and method that allow multiple samples of a liquid in a primary container (here called a 'pouch') to be taken with minimal danger of contaminating the liquid in the container during the sampling process are disclosed. In an embodiment, a closed sterile sight chamber is connected with the pouch in a sterile manner to allow fluid to flow into the chamber while at the same time allowing air within the chamber to be displaced through a bacterial filter to atmosphere. The connection between the sight chamber and the pouch is then terminated (severed or closed), isolating the pouch from the sampling apparatus. Only then are samples of liquid withdrawn from the sight chamber, while allowing air to flow into the chamber through the bacterial filter.

19 Claims, 8 Drawing Sheets

(56) References Cited

U.S. PATENT DOCUMENTS

| | | | |
|---|---|---|---|
| 4,509,566 | A | 4/1985 | Phillips |
| 4,610,670 | A | 9/1986 | Spencer |
| 4,722,732 | A | 2/1988 | Martin |
| 4,917,804 | A | 4/1990 | Franks et al. |
| 4,919,895 | A | 4/1990 | Heldebrant et al. |
| 5,074,839 | A | 12/1991 | Choksi et al. |
| 5,132,026 | A | 7/1992 | Baluyot et al. |
| 5,222,945 | A | 6/1993 | Basnight |
| 5,234,411 | A | 8/1993 | Vaillancourt |
| 5,601,730 | A | 2/1997 | Page et al. |
| 5,702,383 | A | 12/1997 | Giesler et al. |
| 5,776,116 | A | 7/1998 | Lopez et al. |
| 5,858,642 | A | 1/1999 | Cain et al. |
| 6,223,940 | B1 | 5/2001 | Quinn |
| 6,520,948 | B1 | 2/2003 | Mathias et al. |
| 7,785,304 | B2 | 8/2010 | Kashmirian et al. |
| 2002/0185186 | A1 | 12/2002 | Juliar et al. |
| 2003/0028156 | A1 | 2/2003 | Juliar |
| 2003/0176813 | A1 | 9/2003 | Mathias et al. |
| 2003/0199827 | A1 | 10/2003 | Thorne |
| 2004/0009542 | A1 | 1/2004 | Dumont et al. |
| 2011/0139276 | A1 | 6/2011 | Kashmirian et al. |

FOREIGN PATENT DOCUMENTS

| | | |
|---|---|---|
| WO | WO/2004/037156 | 5/2004 |
| WO | WO/2005/048842 | 6/2005 |

OTHER PUBLICATIONS

PCT International Preliminary Report on Patentability dated May 22, 2006 issued in PCT/AU2004/001562 (WO2005/048842).
US Office Action dated Jul. 12, 2007 issued in U.S. Appl. No. 10/990,820.
US Final Office Action dated Apr. 15, 2008 issued in U.S. Appl. No. 10/990,820.
US Office Action dated Feb. 3, 2009 issued in U.S. Appl. No. 10/990,820.
US Final Office Action dated Dec. 8, 2009 issued in U.S. Appl. No. 10/990,820.
US Notice of Allowance dated Apr. 22, 2010 issued in U.S. Appl. No. 10/990,820.
Canadian Intellectual Property Office, Requisition in Application No. 2,545,386, dated Apr. 29, 2009.
US Office Action dated Apr. 3, 2013 issued in U.S. Appl. No. 12/857,918.
US Final Office Action dated Dec. 4, 2013 issued in U.S. Appl. No. 12/857,918.
Presentation of material obtained from inventor(s) by representative of ITL Corp. to client of ITL Corp. on May 28, 2003; pp. 1-10.
Images obtained from inventor(s) and sent by representative of ITL Corp. to client of ITL Corp. on Aug. 18, 2003; pp. 1-4.
Images obtained from inventor(s) and send by representative of ITL Corp. to client of ITL Corp. on Sep. 22, 2003; pp. 1-2.
Presentation of material obtained from inventor(s) by representative of ITL Corp. to client of ITL Corp. on Sep. 24, 2003; pp. 1-11.
Brochure containing images obtained from inventor(s), which was made available at AABB meeting (Nov. 2-4) in 2003; One Page.

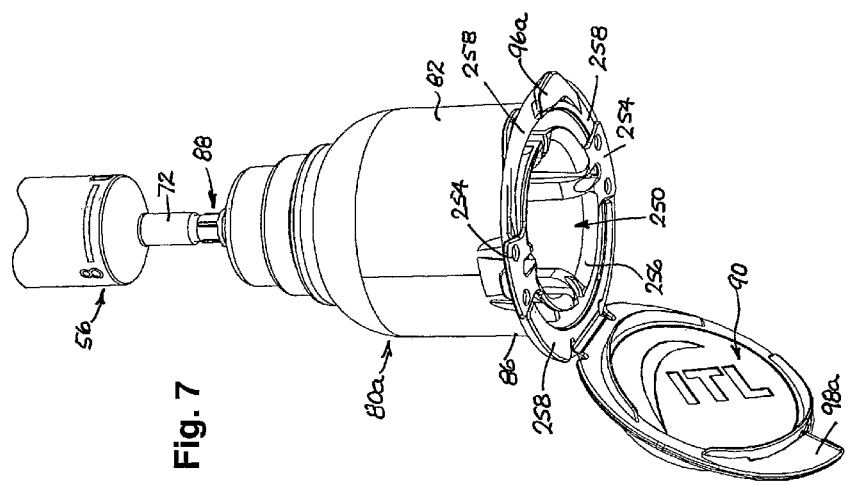

STERILE SAMPLING METHODS AND APPARATUS

CROSS-REFERENCE TO RELATED APPLICATIONS

The current application is a Continuation of co-pending U.S. patent application Ser. No. 12/857,918, filed Aug. 17, 2010, which is a Continuation in Part of co-pending U.S. patent application Ser. No. 10/990,820, filed Nov. 17, 2004, which claims priority from Australian provisional patent application ser. no. 2003906364, filed Nov. 19, 2003.

FIELD OF THE INVENTION

This invention relates to methods and apparatus for the sterile sampling of liquids in containers in ways that minimize the danger of contaminating the liquid in the container by the sampling process. It may be applied to the sampling of platelets and other blood products from collection pouches.

For convenience and without meaning to exclude other forms of containers, the liquid containers to be sampled will herein be called pouches. As it will be normal for the pouch being sampled to be arranged above the sampling apparatus to take advantage of the hydrostatic head thus provided, it will be convenient to refer to parts of the apparatus as being above or below, or as being upper or lower, with respect to other parts. However, the pouch and sampling apparatus could be arranged so liquid flow does not flow under gravity, in which case some parts are likely to be more distal or proximal relative to other parts (with respect to the user). Accordingly, the terms 'upper and 'lower', 'above' and 'below' should be understood as being equivalent to 'distal and 'proximal' (respectively) as used herein.

BACKGROUND OF THE INVENTION

There are occasions in medical practice where it is desirable to check the sterility or other properties of a liquid stored in a pouch before that liquid is administered to a patient or otherwise used. Examples are blood and blood components such as serum and platelets. The US blood industry association, the American Association of Blood Banks (AABB), an association that is globally recognized, recently updated the technical requirements for blood collection, storage and testing and has included a new pre-transfusion QC requirement that will go into effect in March 2004. The new QC test requirement involves testing stored platelets for evidence of bacteria. If bacteria are detected in a unit (i.e., a pouch) of platelets, that unit will not be eligible for transfusion. In order to perform the necessary tests, multiple samples of platelets are usually extracted from the platelet container into respective sample phials. In some cases samples from multiple pouches are mixed and then tested. However, there is serious danger that the sampling procedure itself can introduce bacteria into the pouch liquid.

The pouches usually have attached plastic filling tubes that have been heat-sealed. To take a sample, a sharp hollow steel needle attached to a syringe can be inserted into the filling tube and some of the liquid withdrawn before the needle pulled out of the tube. Desirably, the filling tube can be heat-sealed again between the pouch and the puncture point. Some pouches are provided with 'needleless ports', which have septums that can be penetrated by blunt cannulae attached to syringes. In either case, bacteria can be introduced into the pouch during the sampling process and/or by subsequent entry through the puncture site. The use of a blunt cannular with a needleless port not risks introducing bacterial into the pouch but it normally does not allow for subsequent heat-sealing to isolate the port. Of course, collecting samples by using a needle to puncture the thin wall of the pouch itself offers the worst alternative because of the likelihood that, after withdrawal of the needle, the thin wall of the pouch will not seal sufficiently to prevent the ingress of bacteria through the puncture site.

SUMMARY OF THE INVENTION

The present invention provides methods that allow multiple samples of a liquid in a primary container (here called a 'pouch') to be taken with minimal danger of contaminating the liquid in the container during the sampling process. The method involves connecting a closed sterile sight chamber with the pouch in a sterile manner to allow fluid to flow into the chamber while at the same time allowing air within the chamber to be displaced through a bacterial filter to atmosphere. The connection between the sight chamber and the pouch is then terminated (severed or closed), isolating the pouch from the sampling apparatus. Only then are samples of liquid withdrawn from the sight chamber, while allowing air to flow into the chamber through the bacterial filter. Though there may still be risk of contamination of liquid in the sight chamber as samples are withdrawn, such contamination cannot carry through to the liquid in the pouch.

Where the pouch is provided with a sealed flexible thermoplastic outlet tube, a similar inlet tube is connected to the chamber and a connection between the outlet tube and the inlet tube is preferably effected by 'sterile-docking' the outlet tube and the inlet tube to establish sterile connection therebetween. [Sterile-docking is a known technique and is disclosed, for example, in U.S. Pat. No. 4,369,779 to DuPont.] However, the method of the invention preferably includes the steps of closing (e.g., by clamping) the inlet tube below the point where the sterile-docking is to take place, releasing the clamp after the sterile-docking has been effected to allow a quantity of liquid to flow from the pouch to the chamber, re-closing the inlet tube to stop liquid flow and then heat sealing both the pouch outlet tube and the chamber inlet tube (allowing the docked portion of these tubes to be discarded). Alternatively, where the pouch is only provided with a septum port, the chamber inlet tube can be fitted with a blunt-tipped cannular adapted to enter that port to establish the connection between the pouch and the chamber in a substantially sterile manner. While the clamping and unclamping procedure just indicated can also be followed with advantage, the connection between the pouch and the sight chamber should be terminated by withdrawing the cannular before samples are drawn-off from the sight chamber.

The method may also include entering evacuated sample phials into a cup-like sample port (which has a sheathed needle that is connected to the chamber) to effect the withdrawal of portions of the liquid in the chamber as separate samples. Since the needle is sheathed, the outlet of the sight chamber is sealed until the first sample is taken so there is minimal danger of contamination of the pouch liquid via the chamber. Since all samples are drawn-off while the chamber is disconnected from the pouch, there is no danger that the sample gathering procedure will contaminate the liquid in the pouch and there is only a very slight danger that the sampling procedure will contaminate liquid within the chamber or the samples. The sample port can be rigidly attached to the sample chamber so that the chamber can be held vertical and in view by gripping the sample port in one hand while inserting successive files into the port with the other hand.

The sight chamber can be conveniently formed from the transparent barrel of a medical syringe having volume graduations so that the amount of liquid withdrawn in each sample can be judged and controlled. Though the use of a flexible-walled bag-like chamber is also envisaged, it is not preferred.

As liquid may flow into the chamber too quickly when the pouch is connected, or be may be withdrawn too quickly from the chamber when a phial is inserted into the sample port, the method may include the step of at least partially closing the chamber vent to regulate the rate of egress or ingress of air from and to the chamber. A hinged cap may be provided for closure of the chamber vent and can be used for the function indicated. Of course, the rate of inflow of liquid from the pouch to the chamber can also be regulated by the use of a clamp valve fitted to the inlet tube.

From another aspect, the invention comprises apparatus for use in dispensing samples of liquid drawn from a pouch in a sterile manner, the apparatus including a sight chamber with inlet means, such as the aforementioned thermoplastic inlet tube, for conveying liquid from the pouch to the chamber under sterile conditions. The chamber also has outlet means adapted to permit flow of liquid from the chamber in one or more samples. A filtered vent is provided in the chamber to permit displaced air to flow from the chamber when liquid flows therein and to permit air to flow into the chamber when liquid flows therefrom, the filtered vent serving to block passage of airborne particles including bacteria into the chamber. Valve means (such as a tube clamp) can be provided in association with the inlet means to control flow of liquid into the chamber and also to isolate the chamber from the pouch.

The sample dispensing means is preferably the aforementioned sample port, which is preferably rigidly connected to the lower end of the sight chamber. The sheathed needle of the sample port preferably has a threaded hub by which it is screwed into the closed end of the sample port from the outside, the needle hub preferably being inhibited from unscrewing by ratchet means operable between the hub and the closed end of the port. The sample port may have a hinged cap for closing the open end against accidental intrusion of the finger of a user into contact with the needle point.

The cap preferably includes locking means whereby it can be held closed after use of the sample port and, if necessary, reopened for the insertion of another phial or bottle. The locking means can comprise a tab or catch on the cap that engages with a hole or abutment on the body of the port, or it may comprise flanges on the cap and body that engage with one another in the manner of the catch of a purse.

The apparatus may include a tubular spacer that slidingly fits into the open end of the sample port for the purpose of guiding phials that are of much smaller diameter than the port. The spacer may include radially extending tabs by which it may be gripped between a thumb and finger of a user so that these digits cannot enter the sample port when the spacer is inserted. The spacer is adapted to clip to or snap onto or into the sample port, preferably in such a way that it can be removed from the port (if desired) by again holding the tabs between thumb and finger.

Apparatus of this type may be incorporated in products by manufacturers of blood collection packs, aphaeresis kits, urinary catheter kits, plural and abdominal cavity aspiration kits and the like. In such applications the inlet tubes would be attached by the manufacturer to the kits and it would not be necessary for the user to make the initial connection. However, it may be preferred to employ a frangible connector in the inlet tube to effect the initial connection between the source of the sample liquid and the sterile sampling apparatus of the present invention. In one particular application, the inlet tube, chamber and sample port may be attached to the platelet pouch of an aphaeresis kit by the kit manufacturer without the need for separate sterile packaging. The port would then be immediately ready for use in drawing samples from the pouch without the need for separate sterile docking procedure.

BRIEF DESCRIPTION OF THE DRAWINGS

FIG. 2A is an enlarged perspective sectional view of the sample port of the apparatus of FIG. 2 taken on section plane II-II of FIG. 2.

FIG. 4A is an enlarged view of the blunt cannular used in the modified apparatus of FIG. 4.

FIG. 6 is a perspective view of the sample port of the apparatus illustrated in the previous Figures and a spacer element for use therewith.

FIG. 7 is a perspective view of the sample port of FIG. 6 with the spacer element inserted into the sample port.

DETAILED DESCRIPTION OF THE PREFERRED EMBODIMENT

Figure 1:
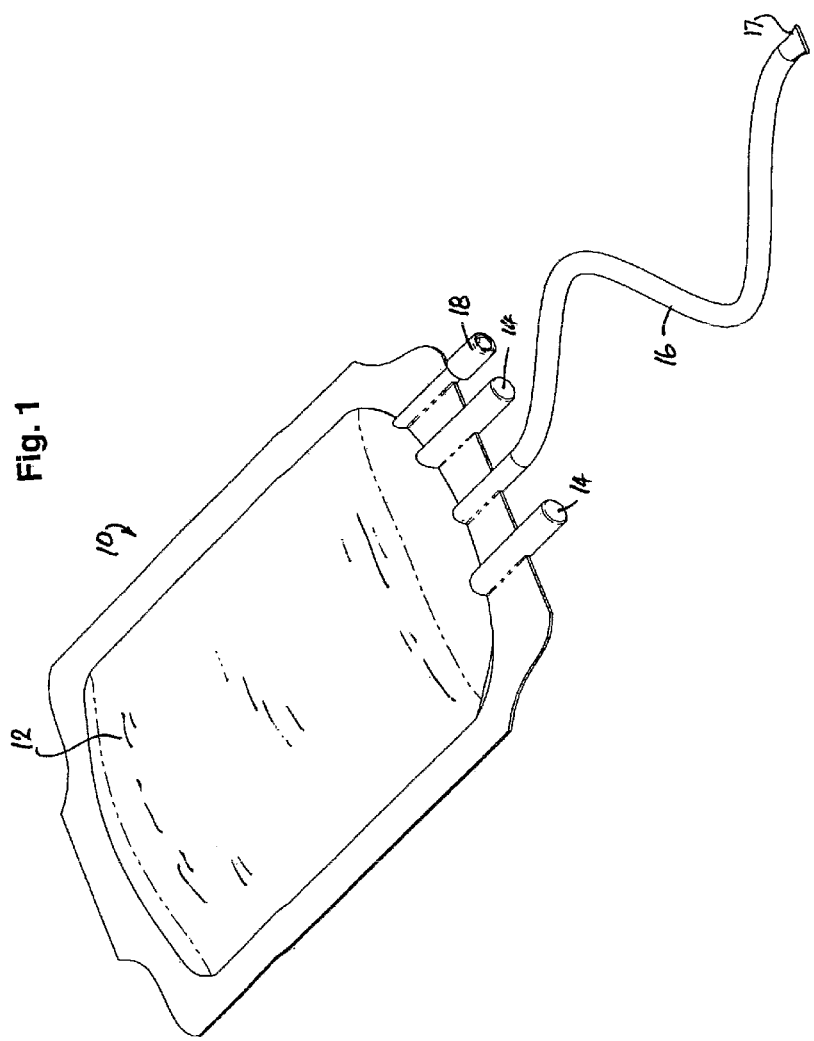
FIG. 1 is a perspective view of a conventional blood or platelet pouch.

FIG. 1 shows a liquid container comprising a conventional sealed plastic pouch 10 containing a unit of platelets liquid, generally indicated at 12. Pouch 10 may have blanked-off tube connections 14 that may have been used during collection of the platelets but it will generally have at least one attached outlet or pouch tube 16 that is heat-sealed at its free end 17. Pouch 10 may also be provided with a split-septum needless port 18 through which a hollow blunt cannular can be inserted to extract samples of liquid 12. Samples of liquid may also be drawn from tube 16 by the use of a syringe and sharp medical needle. As already noted, both these methods of withdrawing samples involve contamination risk, both to the extracted sample and to the liquid in the pouch.

Figure 2:
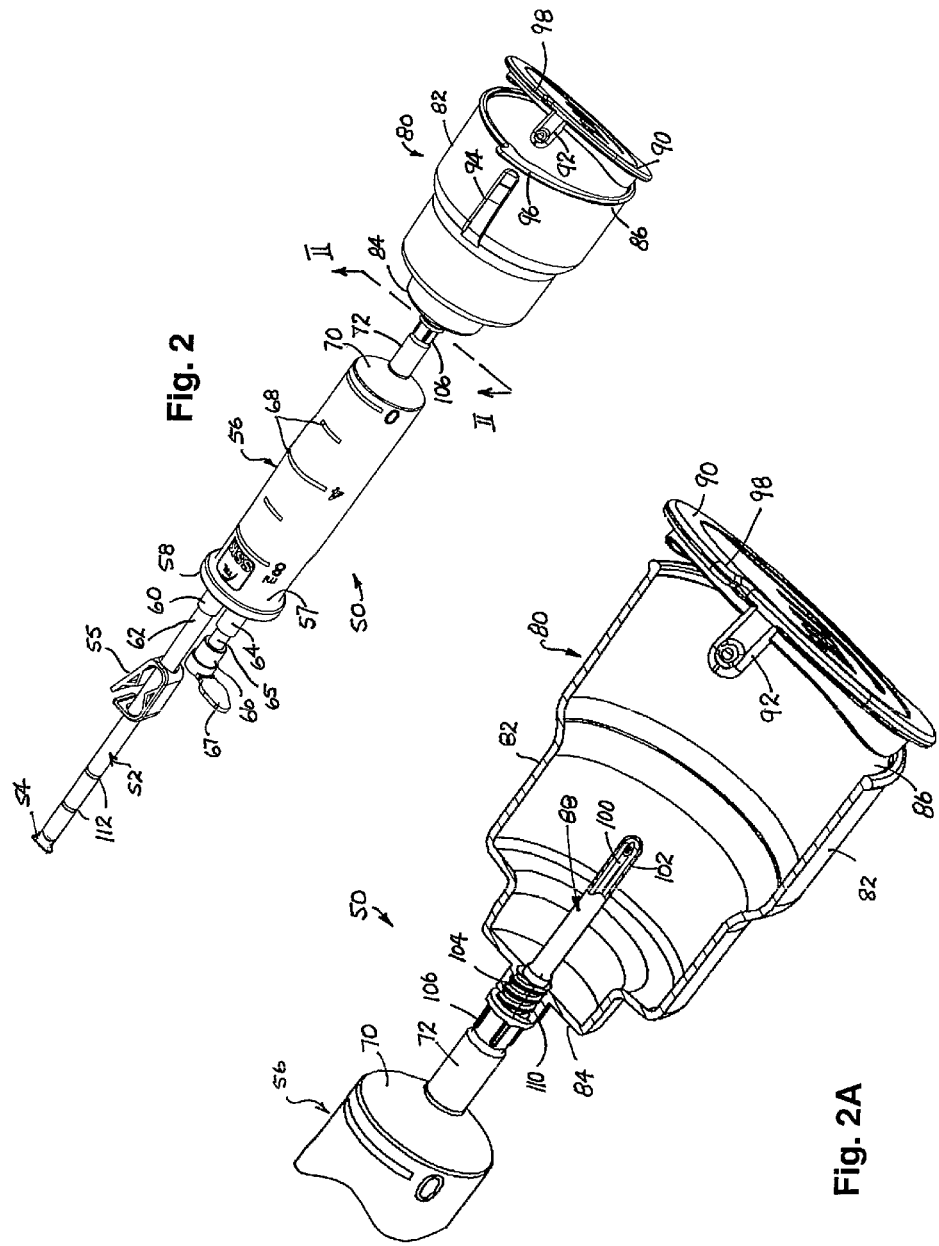
FIG. 2 is a perspective view of the sampling apparatus of the preferred embodiment.

Turing now to FIGS. 2, 2A and 3, the apparatus 50 of the preferred embodiment will now be described. Apparatus 50 is preferably supplied as a sterile unit. It has a plastic inlet or sample tube 52 that is that is heat-sealed at its free upper (or distal) end 54 and is fitted with a pinch clamp 55, which is shown in the open position in which tube 52 is not pinched or blocked. Apparatus 50 also includes a tubular transparent and semi-rigid sight chamber 56 that has an open upper or distal end 57 closed by a closure 58 that has a first tubular spigot 60 connected to the lower or proximal end 62 of sample tube 52 and a second tubular spigot 64 that forms or is connected by a short tube 65 to a filter 66 though which chamber 56 can be vented to atmosphere. Filter 66 is fitted with bacterial filter media (not shown) that allows air to pass but blocks the passage of bacteria, such filter media being known in the art and being commercially available. Preferably, a hinged cap 67 is attached to filter 66 so that the open end of filter 66 can be sealed, if desired.

Sight chamber 56 is conveniently formed from the transparent barrel of a conventional medical syringe that has appropriate volume graduations 68 and a tapered lower or proximal end 70 that terminates in an external spigot-like female Luer socket 72.

A sample port assembly 80 is rigidly connected to Luer socket 72, port assembly 80 comprising (i) a cup-like hollow cylindrical body 82 having a closed upper or distal end 84 and an open lower or proximal end 86 and (ii) a sampling needle assembly 88 (FIG. 2A) screwed into upper end 84 of body 82 so as to extend coaxially therein. Body 82 is preferably molded from plastic with an integrally hinged cap 90 attached to its lower or proximal end 86. Hinged cap 90 is provided with a locking tab 92 that engages with a slot 94 in the side of body 82 so that the cap 90 is held in the closed position to prevent inadvertent contact between the fingers of a user and needle assembly 88 in body 82. Lower end 86 of body 82 and the periphery of cap 90 are provided with outwardly extending flanges 96 and 98 respectively by which the cap can readily pried open again, if desired, between the user's finger and thumb.

Figure 3:
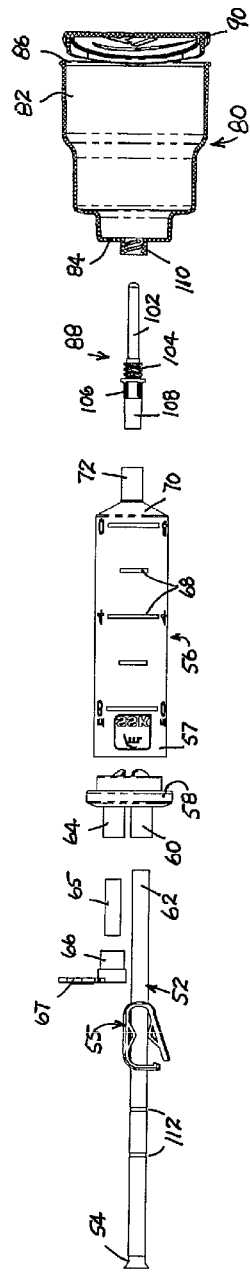
FIG. 3 is a side elevation of the apparatus of FIG. 2 with the principal components shown separated from one another, the sample port also being shown in section, the section plane being indicated at II-II in FIG. 2.

Referring particularly to the enlarged drawing of FIG. 2A, sampling needle assembly 88 comprises a pointed hollow steel needle 100 that is surrounded by a rubber-like sheath 102 and is supported by a molded externally threaded hub 104 having an upper or distal end 106 formed with a distal male Luer spigot 108 (see FIG. 3). Male Luer spigot 108 engages with female Luer socket 72 to form a rigid connection between sample port assembly 80 and sight chamber 56. Hub 104 is screwed into a hollow boss 110 formed in distal or upper end 84 of body 82.

The assembled sampling apparatus 50 is normally shipped as a unit in a sterile pack with vent cap 67 and port cap 90 closed. This minimizes the danger that the edges of the caps will penetrate the packaging during handling. The supply of apparatus 10 with vent cap 67 closed allows sight chamber 56 to remain sealed to atmosphere until sample tube 52 has been docked with pouch tube 16. Similarly, the supply of apparatus 50 with port cap 90 closed ensures that a finger of a user cannot enter port 56 while apparatus 50 is being handled or coupled to pouch 10. Such contact would be likely to cause the point of needle 100 to puncture sheath 102 thus breaking the seal to the chamber via its outlet. Pinch clamp 55 is normally fitted in the open position so that the risk of permanently kinking inlet tube 52 is minimized.

To ready the assembly 50 for use after removal from its pack (not shown), caps 67 and 90 are opened and clamp 55 is closed. Inlet or sample tube 52 is then placed along side pouch tube 16 in a sterile clocking jig, the preferred area for sterile docking being indicated by spaced markings 112 on sample tube 52. The sterile docking procedure is then performed in the normal manner, simultaneously cutting off the sealed ends of tubes 16 and 52 and connecting the severed ends of these tubes together for fluid communication (as described above). Clamp 55 and vent cap 67 are then opened to allow the desired amount of liquid to flow from pouch 10 into sample chamber 56, after which clamp 55 is closed to stop further flow. Flow of liquid 12 from pouch 10 will normally occur under gravity and/or with slight pressure on pouch 10, the flow being assisted by the open vent 66 that allows the air within sight chamber 56 to be displaced. Hence, apparatus 50 will normally be arranged substantially vertically and below pouch 10, with sample tube 52 uppermost and sample port 80 lowermost. This allows the amount of sample liquid in sight chamber 56 to be accurately determined by reference to graduations 68 before clamp 55 is operated to close sample tube 52. Preferably, at this stage, pouch tube 16 is heat-sealed and severed above the docking point and sample tube 52 is heat sealed and severed below the docking point, the docked connection then being discarded. This keeps sampling apparatus 50 sealed and sterile during collection of the sample liquid in sight chamber 56, except for the egress of displaced air though bacterial filter 66. Sample port cap 90 is then prized open by using flanges 96 and 98 to ready apparatus 50 for dispensing of individual sample portions of the sample liquid held in sight chamber 56.

With assembly 50 held generally vertically, preferably by gripping sample port 80 in one hand, vacuum bottles or phials (not shown) are entered upwards into body 82 from open lower end 86 and pushed onto sheathed needle assembly 88 so that needle 100 pierces the sheath 102 and passes through the soft bung of the bottle or phial to suck portion of the liquid in chamber 56. As soon as the desired amount of liquid has been removed, the bottle or phial is pulled from needle assembly 88 and sample port 80, leaving sheath 102 to re-cover needle 100. Successive samples can be quickly and conveniently taken in this way using successive phials or bottles. If desired, port cap 90 can be moved to the closed position between each sample.

Where a liquid with lower viscosity than platelets, or where a large gauge sampling needle 100, is employed, the flow of liquid from sight chamber 56 to the sample phial or bottle may be too fast to accurately judge the portion required for each phial. The flow rate can be reduced by at least partially closing the opening of vent 66 with a finger or thumb or with cap 67. When sufficient samples have been extracted, or when chamber 56 has been emptied, assembly 50 can be discarded using an appropriate disposal container. Before doing so, however, port cap 90 should be snapped closed to mitigate possible contact between a finger of the user and needle 100 and vent cap 67 should be closed to prevent seepage of liquid from the vent.

Figure 4:
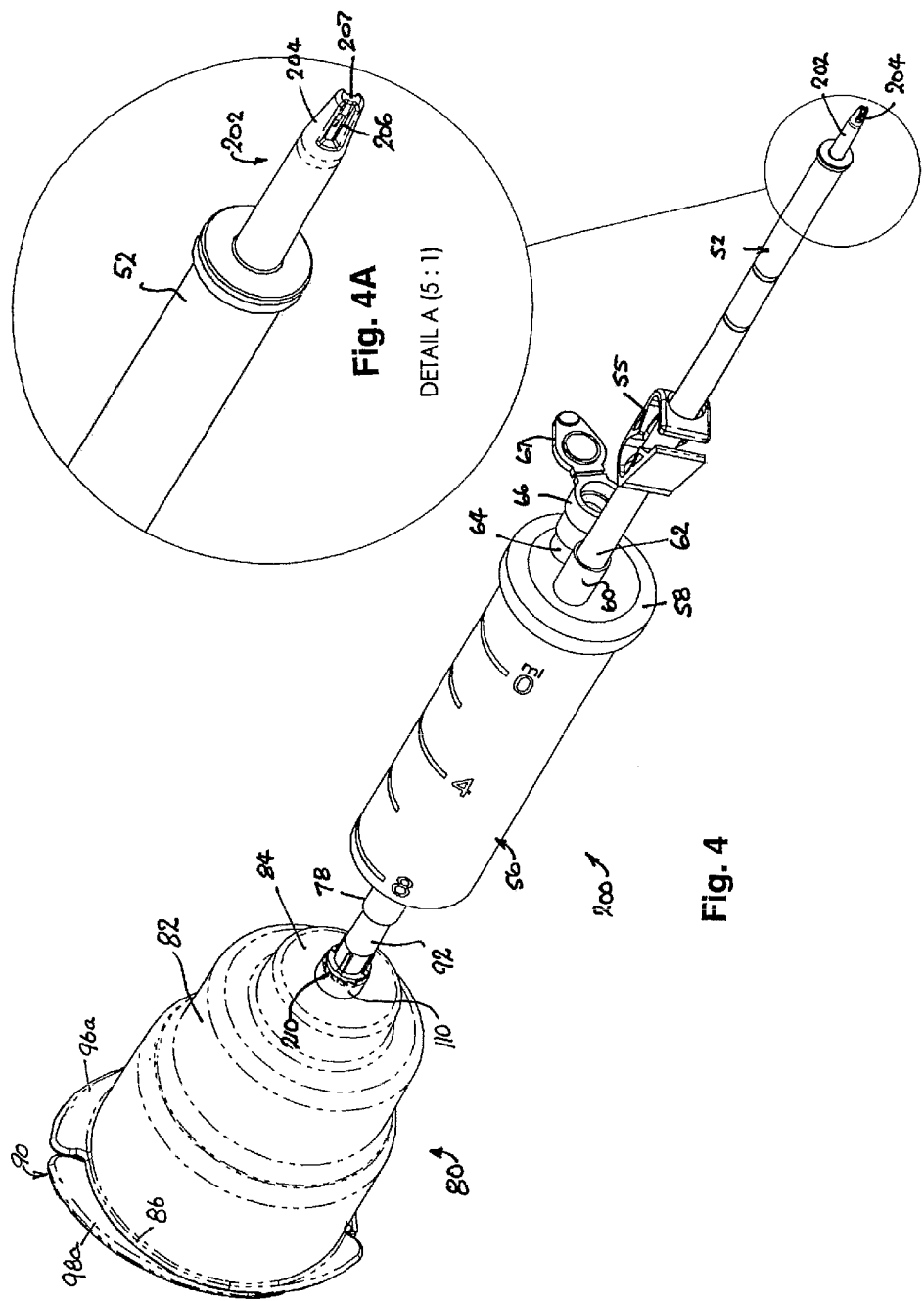
FIG. 4 is a perspective view of the apparatus of FIGS. 1-3 modified in a first way that allows the use of a blunt cannular to access a septum-port in the pouch to be sampled.

Turning now to FIGS. 4 and 4A that illustrate a modified sampling apparatus 200 that is very similar to as apparatus 50 described above except for some particular modifications. Accordingly, those parts of apparatus 200 that are essentially the same as those of apparatus 50 have been assigned the same reference numerals. The first important modification is a blunt cannular 202 fitted to the upper or distal end of sample tube 52 instead of heat-sealed end 54. The cannular tip 204 is of conventional design (and is shown greatly enlarged in FIG. 4A) having side inlet apertures 206 and a non-coring nose 207. The second important modification is in the way that port cap 90 is locked closed. In this case locking tab 92 is omitted together with cooperating slot 94 and the lateral flanges 96a and 98a on open end 86 of port body 82 and on cap 90 (respectively) are modified so that they can snap together in the closed position like the closure commonly used in ladies purses. The omission of tab 92 simplifies the molding procedure and the omission of slot 94 reduces the possibility of liquid dripping from port body 82.

A third modification comprises the use of a ratchet-like engagement between the radial face of Luer needle hub 92 and the radial face of a boss 110 on the closed upper end 84 of port 80 in such a way as to inhibit unscrewing of needle assembly 88. In this case, ratchet teeth 210 are formed on the radial face of boss 110.

Another optional modification to apparatus 50 and/or 200 described above is embodied in apparatus 220 of FIG. 5, which apparatus has many components common to the foregoing apparatus, such components again being assigned the same reference numerals. The first modification embodied in apparatus 220 is the replacement of former inlet or sample tube 52 by four sample tubes 52a, 52b, 52c and 52d, each having a heat sealed distal end (54a, 54b, 54c and 54d, respectively) and each having its own clamp (55a, 55b, 55c and 55d, respectively). The lower or proximal ends of tubes 52a, 52b, 52c and 52d are coupled by a four-way connector 222 to inlet spigot 60. Multiple inlet or sample tubes 52a-52d are provided so that liquid can be extracted from respective multiple pouches into common sight chamber 56 and mixed therein before being dispensed to one or more sample phials (not shown) without any possible danger of cross contamination between pouches.

Thus, the advised procedure for generating a mixed sample from multiple pouches is to close all clamps 55a-55d, sterile dock a first pouch to, say sample tube 52a, release clamp 55a to allow a first quantity of liquid to flow from the first pouch to sample chamber 56, close clamp 55a, heat-seal and sever the outlet tube of the first pouch, heat-seal and sever inlet tube 52a above clamp 55a, and then repeat these steps for each pouch and each sample tube (52b-52d) in turn. Thus, at no time would more than one pouch be connected to the apparatus and no outlet tube of a pouch would be docked to a used inlet tube of the apparatus, so cross-contamination between the pouches would be excluded. A possible but less desirable procedure would be to connect more than one pouch to sight chamber 56 via respective inlet tubes 52a-52d and to operate respective clamps 55a-55d, ensuring that only one clamp was open at one time.

Figure 5:
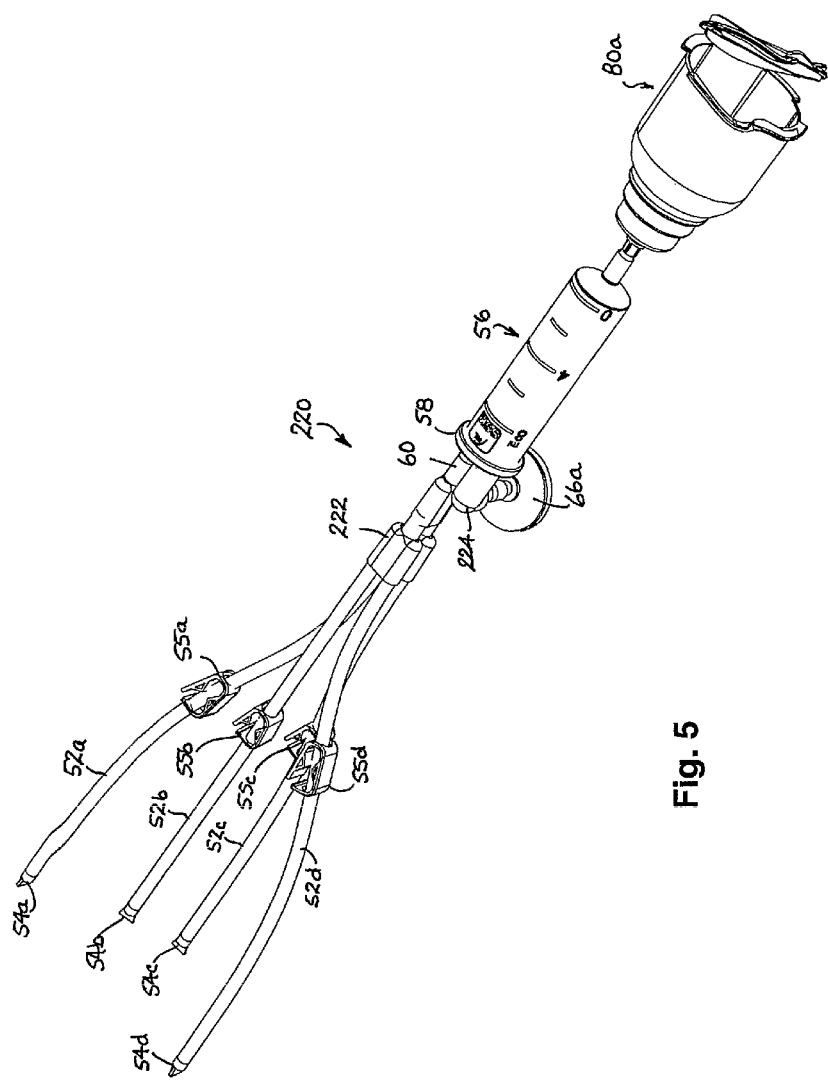
FIG. 5 is a perspective view of the apparatus of FIGS. 1-3 modified to allow samples from multiple pouches to be obtained and mixed before being dispensed to sample phials.

The second modification embodied in apparatus 220 illustrated in FIG. 5 is the use of a large diameter filter housing 66a connected to spigot 64 via an elbow connector 224. The larger housing 66a allows the use of a filter element (not shown) of larger area to provide less restricted air flow and, consequently, to permit more rapid in-flow of liquid into chamber 56 and more rapid draw-off of samples using vacuum phials. The third modification embodied in apparatus 220 relates to sample port 80a and will be described with reference to FIGS. 6 and 7.

FIGS. 6 and 7 show modified sample port 80a adapted for use with a skeletal molded plastic spacer element 250 of generally tubular form that can be pushed upward (as indicated by arrow 252) into body 82 of a modified sample port 80a to allow narrow diameter phials to be reliably aligned with needle assembly 88, larger diameter bottles or phials being aligned by the walls of the port body itself. Spacer element 250 is provided with two radial outwardly-extending tabs 254 on its lower or proximal end 256 and open end 86 of port body 82 is provided with a radial outwardly-extending flange 258 having a pair of opposed notches 260 therein, each notch 260 being proportioned to accommodate respective ones of tabs 254 in a snap fit. The use of outwardly extending tabs that engage the rim portion of open end 86 of port 80a allows spacer element 250 to be inserted by holding it between thumb and finger in such a way that contact between either digit and needle assembly 88 (or the interior of body 82) is strongly inhibited. It will be noted from FIGS. 6 and 7 that sample port cap 90 employs the purse-type snap closure described with respect to FIG. 4, which has inter-engaging radial tabs 96a and 98a on open end 86 of port body 82 and on cap 90 (respectively).

Normally, the user of sampling apparatus having modified sample port 80a and associated spacer 250 will use either large or small diameter phials and, if small diameter phials have been selected, will insert spacer element 250 before the apparatus is connected to pouch tube 16. However, there are occasions where the user is required to collect samples in both small and large diameter phials. This may be necessitated by the destined use of the sample phials or by the type of machines to which they will be coupled. In that event, the user will transfer sample(s) to the large phial or phials before fitting spacer element 250 and, after fitting spacer element 250, then transfer sample(s) to the smaller phial or phials. In the event that a mistake is made and spacer element 250 is inserted before all large diameter phials have been filled, the user can remove spacer element 250 by gripping the edges of tabs 254 and squeezing them together to unlatch them from their respective notches 260. Again, it will be noted that this action is effected without the need for the user to put a finger into spacer 250 or body 82 of port assembly 80.

Figure 8:
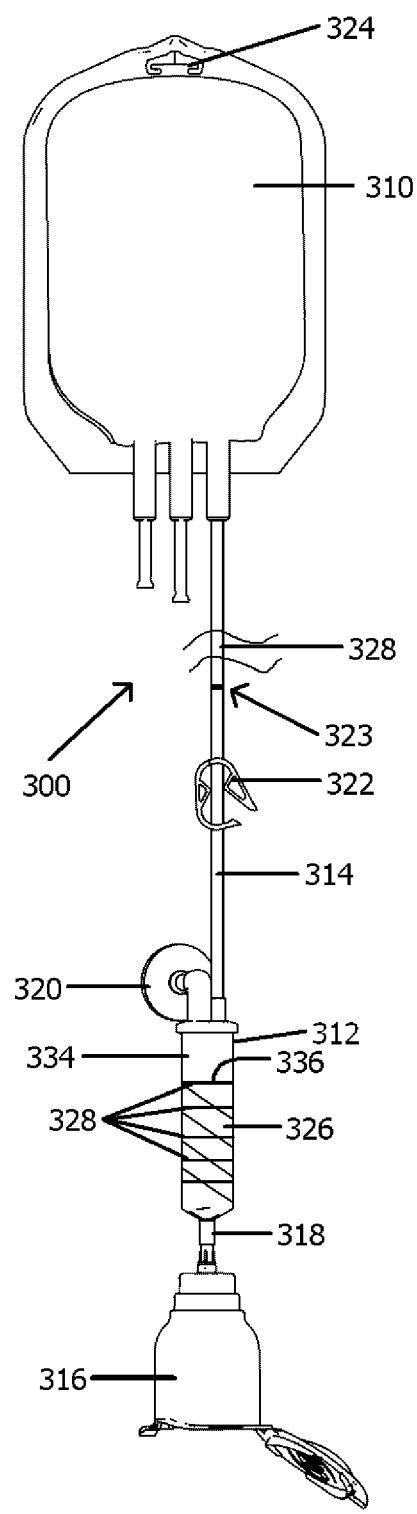
FIG. 8 is a side view of a further embodiment of the invention.
Figure 9:
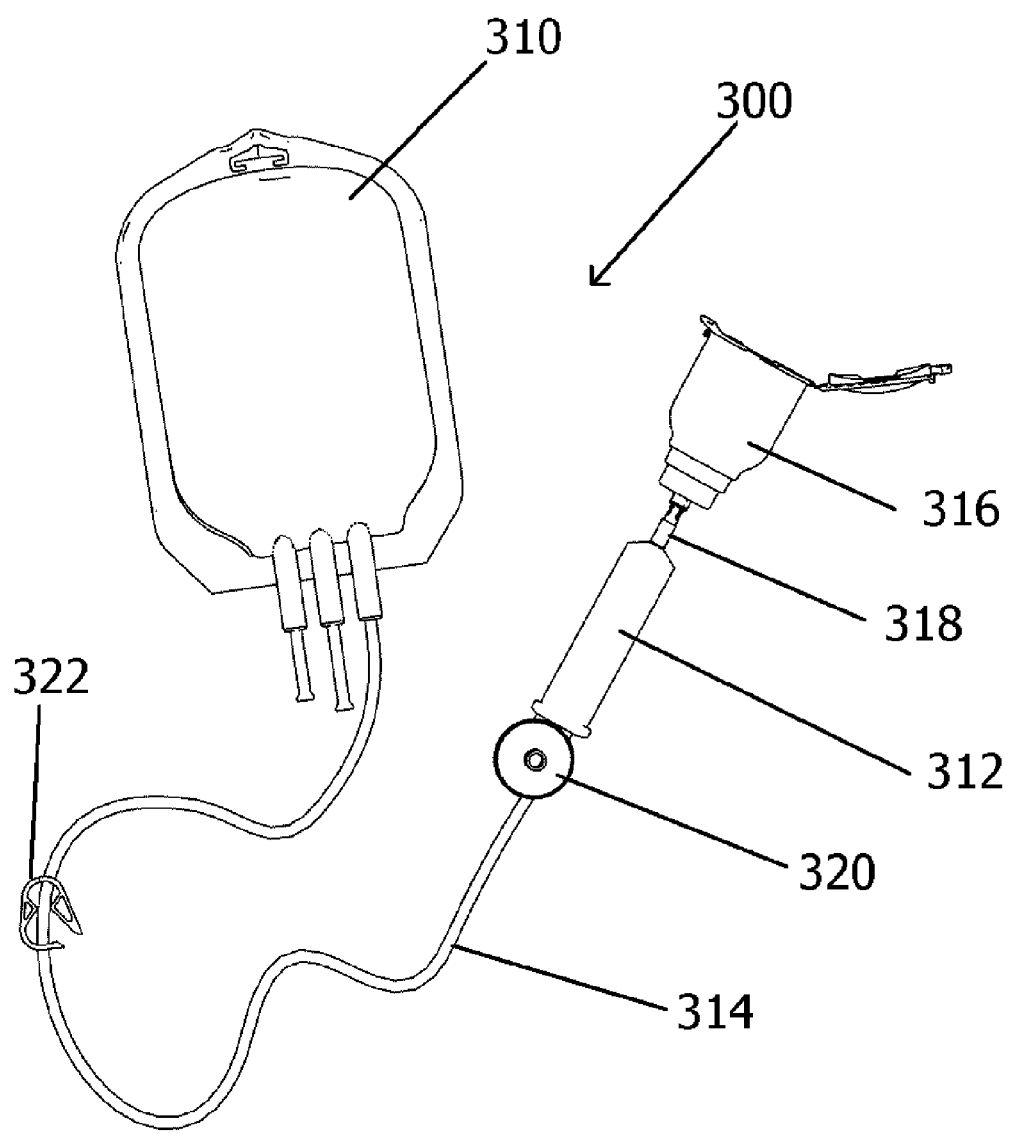
FIG. 9 is another side view of the FIG. 8 embodiment.

Referring to FIGS. 8 & 9 there is shown an assembly 300 according to a further example of the invention. The assembly 300 comprises a combined pouch 310 (typically a platelet container), sight chamber 312 and sampling port 316 arrangement. The pouch 310 is connected to a sight chamber 312 via tube 314. Sampling port 316 is mounted on outlet 318 of sight chamber 312. The sight chamber 312 and sampling port 316 are substantially as the sight chamber 56 and sampling port 80 as shown in FIGS. 2 to 4a, albeit having a large diameter filter housing 320 similar to filter housing 66a of FIG. 5. The sampling port 316 may be used with the spacer element 250 shown in FIGS. 6 and 6a.

A tube clamp 322 is located on the tube 314 intermediate the pouch 310 and sight chamber 312.

The arrangement 300 is manufactured with the tube connected to the pouch 310 and sight chamber 312 such that the end user does not need to make the initial connection between the pouch 310 and the sight chamber 312. During manufacture the arrangement is sterilised. The sampling port may be provided attached to the sight chamber or may be provided in a separate sterile package for attachment by the end user on the outlet of the sight chamber.

As supplied to the end user the tube clamp is preferably closed and so blocks tube 314. Accordingly, until such time as the tube clamp 322 is opened contamination cannot transfer from the sight chamber 312 to the pouch 310. However, a frangible barrier 323 may be provided in the tube 314 that initially closes the tube.

The pouch is filled with a fluid, typically a concentrated platelets mixture derived from whole blood. The exact nature of the fluid is not important and, for example, the arrangement may be used with whole blood.

With the tube clamp 322 or frangible barrier 323 closed the fluid cannot transfer to the sight chamber.

For testing of the fluid in the pouch the assembly is preferably arranged vertically, with the pouch above the sight chamber, as in FIG. 9. Typically this may be achieved by hanging the pouch from a hook or similar via opening 324. The sight chamber 312 and sampling port 318 hang from the pouch. The sight chamber need not hang directly below the pouch and may be raised by a user.

The tube clamp 322 is opened or the frangible barrier 323 opened and fluid flows from the pouch to the sight chamber via tube 314. The amount of fluid 326 in the sight chamber may be measured against graduations 328. As fluid 326 enters the sight chamber air in the sight chamber exits via filter 320.

As seen in FIG. 3, the inlet 330 does not extend downwards from cap 332 significantly and so an air gap 334 may be maintained between the top 336 of the fluid passed into the sight chamber and bottom of the inlet 330. Thus any contamination cannot pass via the fluid in the sight chamber back up the tube 314 to the pouch 310.

When sufficient fluid has passed into the sight chamber 312 the tube clamp 322 is closed, isolating pouch 310 from sight chamber 312. Ideally the tube is heat sealed between the tube clamp 322 and pouch 310, as indicated by 338 before any fluid is removed from the sight chamber. One or more samples are taken from the sight chamber by passing one or more vials into the sampling port and impaling the vial on the needle 100 (shown in FIG. 3) as previously described.

While a preferred embodiment of the invention has been described and illustrated together with some variants, it will be appreciated by those skilled in the art that many other changes can be made without departing from the scope of the present invention as defined by the following claims.

What is claimed is:

1. Apparatus for providing at least one sample of a liquid contained in a pouch while mitigating the danger of contaminating the liquid in the pouch, the apparatus comprising:
    an inlet tube having proximal and distal ends, and comprising a frangible barrier therein, between the proximal and distal ends, the proximal end connected to an inlet of a sterile sight chamber, the chamber comprising:
        a vent in the chamber wall fitted with a bacterial filter through which air can flow to and from the chamber; and
        an outlet;
    the inlet tube comprising a tube clamp thereon, wherein the tube clamp is a sufficient distance from the distal end to permit a sterile fluid connection to be established with the inlet tube at a point distal to the tube clamp;
    the tube clamp operable to regulate liquid flow through the inlet tube to the chamber when the connection is established and operable to block fluid flow in the absence of the connection; and
    a sample port comprising a hollow body with a distal end and a proximal end, wherein the distal end of the sample port is connected to the outlet of the chamber, and the proximal end is opposite the outlet.

2. Apparatus according to claim 1, wherein the inlet tube comprises a flexible thermoplastic inlet tube.

3. Apparatus according to claim 2, wherein:
    the sight chamber is tubular and transparent and has an upper end and a lower end;
    the inlet is located at the upper end, and the outlet is located at the lower end;
    the sample port is joined to the outlet in a rigid manner so that the sight chamber can be supported substantially upright by a user holding the sample port in one hand while inserting a phial into the open end of the sample port with the other hand.

4. Apparatus for providing at least one sample of a liquid contained in a pouch while mitigating the danger of contaminating the liquid in the pouch, the apparatus comprising:
    an inlet tube having proximal and distal ends, and comprising a frangible barrier therein, between the proximal and distal ends, the proximal end connected to an inlet of a sterile sight chamber, the chamber comprising:
        a vent in the chamber wall fitted with a bacterial filter through which air can flow to and from the chamber; and
        an outlet;
    the inlet tube comprising a tube clamp thereon, wherein the tube clamp is a sufficient distance from the distal end to permit a sterile fluid connection to be established with the inlet tube at a point distal to the tube clamp; and
    the tube clamp operable to regulate liquid flow through the inlet tube to the chamber when the connection is established and operable to block fluid flow in the absence of the connection wherein:
        the sight chamber is tubular and transparent and has an upper end and a lower end;
        the inlet is located at the upper end, and the outlet is located at the lower end;
        the vent is located at the upper end;
        the sight chamber is marked with graduations to indicate the volume of liquid therein, the uppermost of the graduations being below the inlet and vent.

5. Apparatus according to claim 1, wherein the vent has an opening to the environment, and a hinged cap is mounted adjacent the opening, the cap movable between a closed position in which the cap blocks the opening and an open position in which the opening is unblocked and positions therebetween in which the opening is partially blocked.

6. Apparatus according to claim 1, wherein the chamber is transparent and rigid.

7. Apparatus according to claim 1, wherein the inlet tube is attached to a platelet pouch of an aphaeresis kit.

8. Apparatus for providing at least one sample of a liquid contained in a pouch while mitigating the danger of contaminating the liquid in the pouch, the apparatus comprising:
    an inlet tube having proximal and distal ends, and comprising a frangible barrier therein, the proximal end connected to an inlet of a sterile sight chamber that is transparent, the chamber comprising:
        a vent in the chamber wall fitted with a bacterial filter through which air can flow to and from the chamber; and
        an outlet;
    the inlet tube comprising a tube clamp thereon, wherein the tube clamp is a sufficient distance from the distal end to permit a sterile fluid connection to be established with the inlet tube at a point distal to the tube clamp;
    the tube clamp operable to regulate liquid flow through the inlet tube to the chamber when the connection is established and operable to block fluid flow in the absence of the connection; and
    a cup-like sample port having an open end and a tubular peripheral wall connected to the outlet of the chamber in a rigid manner, wherein the open end is opposite the outlet.

9. Apparatus according to claim 8, wherein the inlet tube is attached to a platelet pouch of an aphaeresis kit.

10. Apparatus according to claim 1, wherein the sample port has a cup-like shape.

11. Apparatus according to claim 1, wherein the sample port comprises a hollow needle within the body of the sample port, the needle being attached to the distal end of the sample port body.

12. Apparatus according to claim 11, wherein the needle is sheathed.

13. Apparatus according to claim 1, wherein the sample port comprises a cap for closing the proximal end of the sample port.

14. Apparatus according to claim 4, wherein the chamber is rigid.

15. Apparatus according to claim 4, wherein the inlet tube is attached to a platelet pouch of an aphaeresis kit.

16. Apparatus according to claim 8, wherein the chamber is transparent and rigid.

17. Apparatus according to claim 16, wherein the sample port comprises a hollow needle within the body of the sample port, the needle being attached to the distal end of the sample port body.

18. Apparatus according to claim 17, wherein the needle is sheathed.

19. Apparatus according to claim 18, wherein the sample port comprises a cap for closing the proximal end of the sample port.

* * * * *